US006575893B2

United States Patent
Feucht

(10) Patent No.: US 6,575,893 B2
(45) Date of Patent: Jun. 10, 2003

(54) MAGNETIC FIELD APPLICATOR FOR HEATING MAGNETIC SUBSTANCES IN BIOLOGICAL TISSUE

(75) Inventor: Peter Feucht, Berlin (DE)

(73) Assignee: MFH Hyperthermiesysteme GmbH, Berlin (DE)

( * ) Notice: Subject to any disclaimer, the term of this patent is extended or adjusted under 35 U.S.C. 154(b) by 137 days.

(21) Appl. No.: 09/764,517

(22) Filed: Jan. 18, 2001

(65) Prior Publication Data

US 2001/0011151 A1 Aug. 2, 2001

(30) Foreign Application Priority Data

Aug. 7, 1999 (DE) .......................... 199 37 493

(51) Int. Cl.$^7$ .............................. A61N 2/10; H05B 6/10
(52) U.S. Cl. .............................. 600/13; 600/9; 607/103; 607/115; 219/632; 219/670; 219/677; 336/60
(58) Field of Search .............................. 600/13, 14, 15, 600/9, 10; 607/103, 115, 154; 219/670, 632, 635, 647, 672, 677; 336/60

(56) References Cited

U.S. PATENT DOCUMENTS

| | | | |
|---|---|---|---|
| 4,673,781 A | * 6/1987 | Nuns et al. | 219/670 |
| 4,678,883 A | * 7/1987 | Saitoh et al. | 219/670 |
| 5,023,419 A | * 6/1991 | Langstedt | 219/670 |
| 5,197,940 A | 3/1993 | Sievert | 600/9 |
| 5,373,144 A | * 12/1994 | Thelander | 219/670 |

FOREIGN PATENT DOCUMENTS

| | | | |
|---|---|---|---|
| EP | 0 913 167 A2 | 5/1999 | A61N/2/02 |
| FR | 2 508 802 | 1/1983 | A61N/5/02 |

* cited by examiner

Primary Examiner—Philip H. Leung
(74) Attorney, Agent, or Firm—McNair Law Firm, PA; Cort Flint

(57) ABSTRACT

A magnetic field applicator to heat magnetic substances in biological tissue, having a magnetic yoke with two pole shoes across from each other and separated from each other by a distance that defines the magnetic field exposure volume produced by the applicator, and with two magnetic coils, one assigned to each of the two pole shoes, to produce a magnetic field. The magnetic yoke and the pole shoes consist of ferrite segments assembled together. Additionally, the magnetic field applicator is composed of a magnetic yoke having two parallel vertical yoke elements of identical geometry spaced apart a distance from each other, and two transverse yoke elements disposed between said vertical yoke elements. The pole shoes, surrounded by disk-shaped magnetic coils, are attached to the center of said transverse yoke elements and oppose each other over a prescribed distance. One transverse yoke element with surrounding magnetic coil is designed to be an adjustable component relative to the other transverse yoke element in order to adjust the width of the space separating the pole shoes, which defines the magnetic field exposure volume. In this manner an effective and efficient magnetic field applicator is created to carry out hyperthermia treatments and thermo-ablation procedures, as well as having uses in other medical applications.

15 Claims, 5 Drawing Sheets

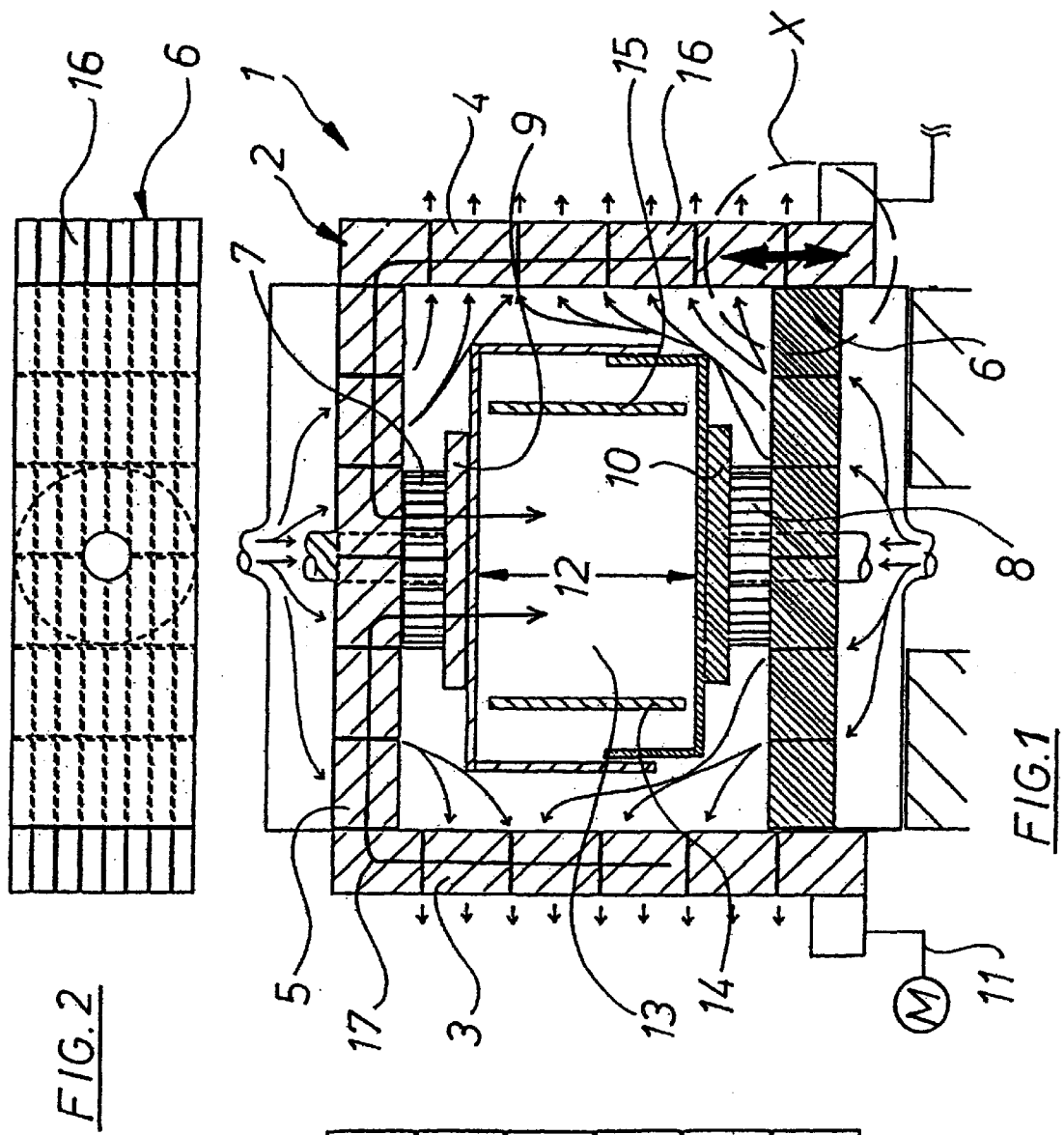
FIG.1
FIG.2
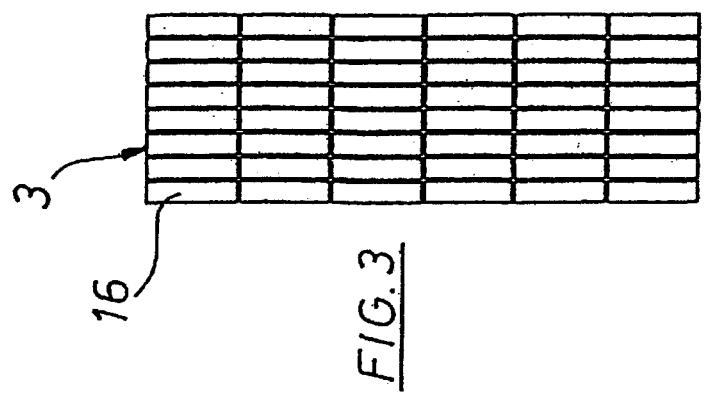
FIG.3

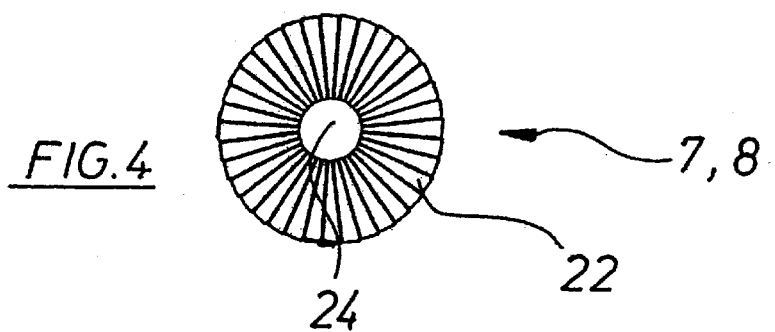
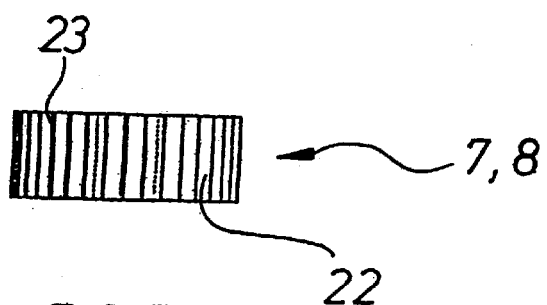
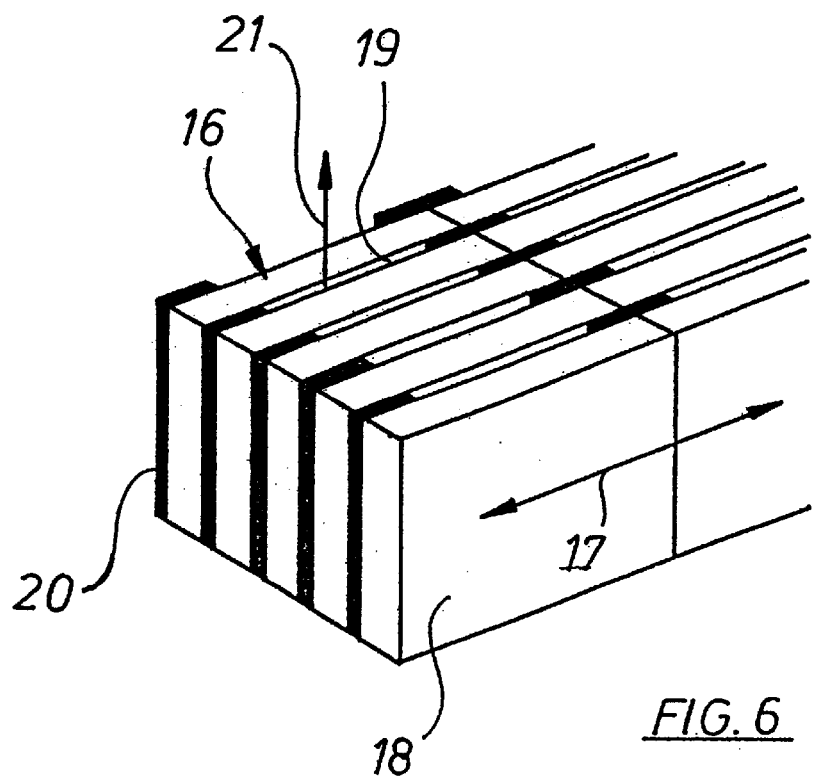

MAGNETIC FIELD APPLICATOR FOR HEATING MAGNETIC SUBSTANCES IN BIOLOGICAL TISSUE

BACKGROUND OF THE INVENTION

The invention relates to a magnetic field applicator for heating magnetic substances in biological tissue for use in administering hyperthermia and thermo-ablation procedures, as well as having other medical and industrial applications.

Cancer diseases are treated in a generally known manner through surgical removal, chemotherapy, radiation therapy or a combination of these methods. Each of these methods is subject to certain limitations, especially at advanced stages following metastasis, when the tumor is located close to critical body areas. In cases of diffused tumor growth with uncertain localization, surgical removal of the tumor is either not possible or offers only minimal chances for a cure. For this reason, surgical intervention is generally combined with radiation therapy and chemotherapy. Radiation therapy is only as precise as the localization of the tumor by means of an image-producing processes, with the utmost care taken to avoid the destruction of healthy tissue. Chemotherapeutic means on the other hand, act systemically over the entire body. With this method, bone marrow toxicity or lack of specificity of the therapy limit the treatment ability. Undesirable side effects and damage to healthy tissue are often the unavoidable consequences with these therapy methods using the present state of the art. Improvement is therefore needed.

Over the last few years, hyperthermia has gained significance as an alternative procedure, which works by heating the tumor tissue to temperatures above 41° C. This process provides an increased success in cancer treatment due to the increased local control, and in combination with surgery, radiation therapy and chemotherapy, improves the chance of survival. With temperatures between 41 and 46° C., and with the natural assistance of the body, a controlled and rather slow reduction of the tumor tissue takes place. Acute destruction of cells starts to take place at higher temperatures starting at 47° C. Depending on temperature, the form of necrosis, coagulation or carbonization, is either called hyperthermia (between 41 and 46° C.) or thermo-ablation (above 47° C.). Until the present invention, hyperthermia systems were considered to be suitable only for the above-mentioned hyperthermia or thermo-ablation procedures, having no other medial applications.

One general problem with hyperthermia systems according to the state of the art, is that no precisely localized and homogenous heating of a target region of a body is, as a general rule, possible. This was possible under certain physiological conditions (e.g. oxygen deprivation, low pH), when the tumor cells become sensitive to hyperthermia, but this only applies in a few isolated circumstances. Hyperthermia by itself is not any more effective on tumor cells than on normal tissue. For this reason, limiting the heating of tissue to the area indicated for treatment (which need not necessarily be confined to the tumor) is especially important, and not realized according to the state of the art. Thus, there is need for improvement.

According to the state of the art, systems dominated by electrical fields, radiate the electromagnetic waves in the megahertz range from antennae or other antenna-shaped objects or arrays of antennae, for regional hyperthermia. For so-called interstitial hyperthermia the electrical field of individual electrical-field applicators is used, and for deep hyperthermia the interference from an antenna array is used. It is a difficulty common to all of these electrical-field-dominated systems that the power consumption of target tissue can only be regulated by means of complex and expensive controls over the electrical field. Furthermore, the heating depends on the electrical conductivity of the applicable target tissue, which is by its very nature heterogeneous, so that an uneven heating of the electrical field is the likely result, even with homogenous radiation. Especially at the transition points of body regions, there is very different electrical conductivity. Excessive power can create "hot spots" that result in pain and burns inflicted on the patient. The consequence is a reduction of the total emitted power necessary for proper treatment of the patient, so that as a result the temperature required to irreversibly damage the tumor tissue (41–42° C.) is not reached in the target region, and the therapy is not successful. Furthermore, due to the interference of dipole arrays, the production of a second electrical field maximum is only possible in areas further inside the body. For physical reasons, the greatest power consumption always takes place at the surface of the body, i.e. at the maximum radius. Added to this is the fact that the blood flow through the tumor and the surrounding normal tissue often changes under hyperthermia, and that this change cannot be compensated for by means of systems dominated by electrical fields from the outside because of the rather low control possibilities over the field.

Other processes according to the state of the art are ultrasound, preferably for thermo-ablation, and interstitial microwave applicators. The latter possess low penetration depth because of the frequency and can therefore only be used in the form of interstitial antennae. In addition, infrared for whole-body hyperthermia is used, as well as extra-corporeal systems to heat body fluids.

Furthermore, a hyperthermia process for the therapy of prostate cancer is disclosed in U.S. Pat. No. 5,197,940, hereinafter the '940 patent, in which "thermoseeds" consisting of magnetic, in particular ferromagnetic or magnetizable material or containing such material, are implanted in the area of the tumor. These thermoseeds are typically several centimeters long, with a diameter in the millimeter range. It is necessary to implant such thermoseeds surgically, and at great cost. During treatment, the thermoseeds are subjected to an alternating magnetic field produced outside a patient's body, whereby heat in the thermoseeds is produced by known hysteresis effects in form of hyperthermia.

These seeds are heated according to the "hot source" principle that while the seeds are heated, the temperatures in the surroundings of the seed drop exponentially, so that the distance between the seeds may not be more than 1 cm in clinical application. In case of greater or uneven distances, thermal under-dosing occurs, which can prevent the success of the therapy. Especially with larger tumors, a very narrow implantation of the seed becomes necessary and the method becomes surgically expensive and stressful to the patient. Aside from the small distance, the seeds must be oriented parallel to the magnetic alternating field for optimal power consumption. The Curie temperature in so-called self-regulating thermoseeds prevents overheating by stopping further power consumption when the ferrite passes into a non-magnetizable state after the Curie temperature has been reached.

The '940 patent discloses the use of a magnetic coil with an oscillatory circuit as the magnetic field applicator for the magnetic alternating field. A patient's body region with the implanted thermoseeds can be placed in the axis of this oscillatory circuit. In practice, air coils are used in the central area where a patient is sitting on a non-magnetizable supporting plate during treatment.

In hyperthermia using thermoseeds, the high cost of surgery and the high intensity of the method, the risk of an imprecise orientation or a change in position of the seeds, the ensuing risk of thermal under-dosing, as well as a limitation of using this treatment method on tumors of smaller size are all disadvantages of this system.

In another known hyperthermia process disclosed in WO 97/43005 for tumor therapy, magnetizable microcapsules are proposed which reach the area of the tumor through the blood stream. In this way surgical implantation of magnetizable elements can be avoided, since with implantation, the danger exists that malignant tumor cells may be dispersed into healthy tissue when a cut is made into the tumor, in addition to the stress that a patient is subjected. A linear magnetic alternating field is used with a frequency in the range of 10 kHz to 500 kHz. The microcapsules are to be used in conjunction with a highly magnetizable material, so that the force of the magnetic alternating field, which is required for the field, can be managed with respect to the instrumentation structure of the required cooling system and the electrical energy supply. A practical instrumentation structure is however not indicated.

In a similar hyperthermia process disclosed in EP 0 913 167 A2, hereinafter EP167, rotating magnetic fields with a frequency greater than 10 kHz are used as fields. To produce the rotating magnetic alternating field, a magnetic field applicator is indicated only sketchily and schematically. The magnetic field applicator comprises a magnetic yoke with two pairs of pole shoes across from each other and separated each other by a gap in the exposure volume and two pairs of magnetic coils assigned to these pole shoes. More specifically, a rectangular magnetic yoke is shown whereby a pole shoe is aligned on the center of the rectangle, starting from the center of each yoke branch, so that a field space is formed. Cylinder coils are mounted on the pole shoes and face each other while being connected to an associated capacitor arrangement to form an oscillatory circuit.

The schematic representation of a magnetic field applicator disclosed in EP167 to carry out the above-mentioned hyperthermia process does not yet lead beyond the experimentation stage to a practical industrial solution, as is required for the sake of favorable production and operating costs, minimal space requirement and low field leakage, and optimal therapeutic effect for utilization under hospital conditions.

It is therefore an object of the present invention to create a magnetic field applicator for heating magnetic substances in biological tissue that produces a tightly focused magnetic field for transferring energy to a targeted tissue area selected for heating and at the same time to prevent unnecessarily heating health tissue.

It is therefore another object of the present invention to create a magnetic field applicator for heating magnetic substances in biological tissue that meet the requirements of cost, space, low field leakage, and effectively controlled heat distribution and conforms to industrial production standards for utilization under hospital conditions and other possible industrial applications.

It is therefore another object of the present invention to create a magnetic field applicator for heating magnetic substances in biological tissue that contains specifically oriented spacing gaps throughout the applicator for the removal of excess heat buildup and to produce a consistent and controlled energy flow for effective heating of the targeted tissue area during treatment.

SUMMARY OF THE INVENTION

The above objectives are accomplished according to the present invention by providing a magnetic field applicator for heating magnetic substances in biological tissue, having a magnetic yoke with two pole shoes across from each other separated by a prescribed space that defines magnetic field exposure volume, and with two magnetic coils, one assigned to each of the two pole shoes to produce a magnetic alternating field.

The magnetic yoke and poles shoes consist of groups of ferrite segments mounted together. Additionally, in the preferred embodiment, the magnetic field applicator is composed of a magnetic yoke having two parallel vertical yoke elements of identical geometry spaced apart a distance from each other and two transverse yoke elements disposed between said vertical yoke elements. The pole shoes, surrounded by magnetic disk-shaped coils, are attached to the center of said transverse yoke elements and oppose each other over a prescribed distance. In order to adjust the width of the space separating the pole shoes that defines the magnetic field exposure volume, one transverse yoke element with surrounding magnetic coil is designed to be an adjustable component relative to the other transverse yoke element. Advantageously, the closure of magnetic flux is subdivided on both sides into two paths of equal length and having the identical geometry. The mechanical aspects of adjusting one transverse yoke element relative to the other in this configuration is easily implemented and much simpler than in a design with only one vertical yoke element, since the two vertical yoke elements can be utilized as supports for either side.

Conducting a hyperthermia procedure, particularly with magnetic liquids, requires magnetic alternating field forces of approximately 15 to 20 kA/m at approximately 50 to 100 kHz. With a magnetic field exposure volume of 8 to 30 L, an effective energy capacity of approximately 18 kW to 80 kW must be produced. Since only a few watt are produced by the magnetic fluid in a patient's body, the energy must be produced at a high-frequency to be able to transmit the necessary heat to effectively treat tumor tissue.

With the arrangement disclosed above it is possible to keep the exposure volume of the magnetic field, as well as any field leakage, advantageously low to limit the exposure to a targeted area in the patient's body that is to undergo therapy. As a result, the required energy expenditure necessary for heat transmission, and ultimately heating tumor tissue, can be reduced. The shape of the magnetic yoke and pole shoes, together with their composition of ferrite segments, contribute to this efficiency by preventing undesirable excesses in flow density and magnetic field losses.

The utilization of ferrite segments in combination with high alternating frequency of approximately 50 to 100 kHz, makes possible an advantageous limitation of the magnetic field exposure volume, whereby only about 1/2000 of the energy, which would have an equivalent air volume, is moved in the ferrite volume. However, ferrite segments are prone to losses, whereby a doubling of the flow density in the work area can result in 5 to 6 times greater field losses. For this reason, appropriate measures are indicated below in order to keep the flow density low, and in particular, to avoid undesirable flow density increases, or at the very least reduce them considerably.

Ferrites are ceramic-like building blocks that can be produced in any desired form at a reasonable cost, and not necessarily in the overall form of the magnetic yoke used here. When combined into segments, these ferrite blocks allow an even energy flow through transitions between other segments and helps avoid flow density changes.

The magnetic field applicator, according to the invention, is equally well suited to carry out hyperthermia treatments and thermo-ablation procedures. In addition, the magnetic field applicator is suitable to warm other substances for medical applications other than in cancer therapy. Among these alternatives are all the heat-related medical applications such as heat-induced implant or stent regeneration, implant or stent surface activation, heating of inflamed body areas not affected by cancer for therapeutic purposes, facilitating contrast media distribution or improvement through magnetic alternating field excitation of super-paramagnetic contrast media, the mobilization of molecular-biological, cell-biological and development-physiological processes through excitation of magnet-carrier-assisted gene transfer systems, ligands, receptors, transmitters, other signal molecules as well as the triggering of material metabolism processes and endocrinal processes.

In the preferred embodiment, a component consisting of a lower transverse yoke element and associated pole shoe with magnetic disk-shaped coil are attached to a fixed position. A patient carriage with a patient support and carriage position display made of a plastic material can also be attached to the fixed pole shoe, whereby the patient need not be moved during the adjustment of the width of the space defining the exposure volume. Relative to this fixed position, a portal consisting of the two vertical yoke elements and the upper transverse yoke element with associated pole shoe and magnetic coil can then be shifted relative to this fixed component by means of a vertical displacement device for the adjustment of the width of the space defining the exposure volume.

A vertical displacement device can be made of a simple linear drive attached, preferably, to a vertical magnetic yoke element. For example, a self-inhibiting spindle drive can be used, so that the overall arrangement can be implemented very reliably and without danger that heavy magnetic yoke components may endanger a patient due to errors in the displacement device.

In a further advantageous development, the magnetic yoke can be held together in a supporting structure through which cooling air may be passed into the applicator and circulated through the cooling-air gap of the ferrite components for heat removal.

Depending on conditions and on special requirements, the space defining the exposure volume, and thereby the volume exposed to a magnetic field, can be limited laterally by field limiting coils and/or by bulkhead walls.

Accordingly, the magnetic field applicator can thus be used for a precisely localized non-contact hyperthermia on all kinds of tissues, bodies and objects incorporating magnetic substances. A preferred application of the magnetic field applicators is in the area of medicine, in particular in cancer therapy, whereby a magnetizable liquid with magnetizable nano-particles is preferably used as the magnetic substance to heat tissue when exposed to the magnetic field. A tumor area is to be heated locally by this method to temperature values above 41° C.

Magnetic alternating fields with magnetic field forces of approximately 10 to 15 kA/m and frequencies from approximately 50 to 100 kHz are used for this purpose. In combination with the magnetic field applicator claimed above, the temperatures required for tumor therapy can then be reached for effective treatment. According to the invention, 1 to 2 kA/m is sufficient in a thermoseed application of the magnetic field applicator. Depending on the given situations, frequencies in a wider range, from 20 to 500 khz, may also be suitable.

In arrangements with cylinder-shaped coils surrounding the pole shoes, inductive heating causes temperatures to rises in the coils last winding that extends to the air space between the pole shoes, requiring extra measures for heat removal. The disk-shaped coil design with at least one winding extending helicoidally and forming an intermediate air gap between the coil and pole shoe, on the other hand, results in considerably lower flow densities on the surrounding edge of the assigned pole shoes, which reduces undesirable increases in flow density and heat buildup.

In one preferred embodiment of the invention, the magnetic disk-shaped coils made of spun copper-strand wire, should have one or more windings that extend helicoidally in order to minimize eddy current energy losses as much as possible.

In an especially advantageous embodiment, the pole shoes are made in a cylindrically shape and aligned facing parallel to each other, with the pole shoe ends opposing each other over a distance that defines the exposure volume. Accordingly, the magnetic disk-shaped coils are made in the form of rings surrounding the pole shoe ends and forming an intermediate air gap. This evens out the magnetic flow and is accompanied by a reduction of excess heating that would otherwise be increased at spatial corners and edges of the pole shoes.

Especially favorable conditions with respect to energy and flow are derived from the magnetic disk-shaped coil being placed as close as possible to the air space defining the exposure volume, particularly in a flush-surface arrangement with the assigned end of the pole shoe surface. Additional optimization is achieved if the intermediate air gap measures approximately 1/10 of the diameter of the pole shoe (0.07 to 0.1 times) and the surrounding edge of the corresponding pole shoe surface is rounded off. In this manner damaging flow density excesses are reduced considerably.

The pole shoe diameter should be greater than the width of the space defining the exposure volume. This results in a reduction of any field leakage outside the pole shoes or the exposure volume of the magnetic field, so that the flow density throughout the ferrite segments, and therefore the losses in the ferrite material, can be kept at a relatively low level. If pole shoes with relatively small cross sections are used, the losses in the ferrite segments would be disproportionally high, making effective treatment of a tissue area difficult.

The magnetic yoke is composed of ferrite segments that have had any outer sintering layers produced during manufacturing removed, and the magnetically conductive surfaces ground flat to created uniform transitions throughout the yoke segments. The round pole shoes are accordingly composed of wedge-shaped ferrite segments like pieces of a cake, with adjoining surfaces also ground flat and freed of sintering layers.

In order to lower eddy current losses, the ferrite segments should be composed of ferrite plates aligned into adjacent rows, each row being separated from the other by plastic spacers defining an insulation/cooling gap. In the assembled state, these ferrite plates are aligned along the magnetic flow direction. To produce one-piece ferrite segments from ferrite plates, the plates are bonded to together via the spacers with adhesive. These ferrite segments are then assembled together to form the magnetic yoke. Also, narrow transition gaps are defined between the ferrite segments creating transitions, which help control the magnetic flow through the yoke and promote efficient heat removal.

Similarly, the wedge-shaped ferrite segments are combined to form the pole shoes, whereby a tubular central bore is left open that allows cooling air to be introduced for heat removal. A temperature-resistant two-component adhesive is preferably used to bond the ferrite plates.

The gaps between the ferrite plates serve as an electrical insulator and cooling channel, when cooling air is passed through the gaps. Cooling is necessary, despite ferrite's low conductivity, since eddy currents are produced that trap in excess heat, which must be removed. Although liquid cooling would be more efficient, this cannot effectively be done in this case. Oil cooling is dangerous because of the flammability of oil, and equivalent non-flammable liquids generally contain toxins. Generally speaking, the density problems, especially with a movable yoke element, in combination with the other technical difficulties, could only be solved by a liquid coolant at high cost.

As indicated above, to have accurate control over the magnetic flow through transitions between ferrite segments, the magnetically inactive sintering layers of approximately 0.1 to 0.2 mm produced in the manufacturing process must be removed, and the magnetically conductive surfaces ground flat. Due to the high permeability of ferrite, the more even the surface, the better flow control there is between transitions of the magnetic yoke. It is especially advantageous to have forced-air gaps of approximately 2 to 3 mm between the transitions of the transversely movable yoke elements and adjoining vertical yoke elements, and at transitions between transverse yoke elements and the pole shoes, to help control the magnetic energy flow. In order to reduce the manufacturing costs and depending on conditions, a sintering layer may be left in a ferrite segment when placed in the vicinity of a relatively wide forced-air gap.

DESCRIPTION OF THE DRAWING

The apparatus and method to carry out the invention will hereinafter be described, together with other features thereof. The invention will be more readily understood from a reading of the following specification and by reference to the accompanying drawing forming a part thereof, wherein an example of the invention is shown by way of illustration and not limitation and wherein:

FIG. 1 shows a schematic sectional view through a magnetic field applicator;

FIG. 2 shows a schematic top view on the magnetic field applicator of FIG. 1;

FIG. 3 shows a schematic side view of the magnetic field applicator of FIG. 1;

FIG. 4 shows a top view on a pole shoe with wedge-shaped ferrite segments;

FIG. 5 shows a side view of the pole shoe of FIG. 4;

FIG. 6 schematically shows a perspective and enlarged representation of the structure of the cut-stone-shaped ferrite segments;

DETAILED DESCRIPTION OF THE INVENTION

Figure 7:
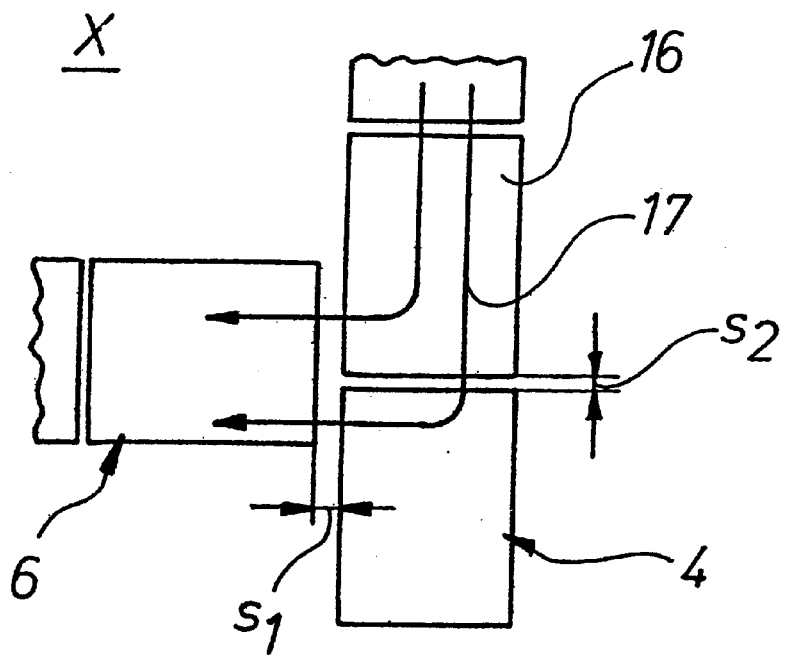
FIG. 7 schematically shows an enlarged representation of a transitional area between a vertical yoke element and a transverse yoke element.

Referring now in more detail to the drawings, an illustrative embodiment of the invention will now be described. In FIG. 1, a magnetic field applicator 1 for hyperthermia is shown, into which a body with a magnetic substance can be introduced and subjected to magnetic alternating fields and irradiated. A tumor zone in human body tissue, into which a liquid with magnetic nano-particles is incorporated, is especially well suited to be exposed to the magnetic fields, and whereby the tumor zone can be heated to temperature values above 41° C., destroying the tumor.

The magnetic field applicator 1 comprises a magnetic yoke 2 designed with two parallel vertical yoke elements 3, 4 at a distance from each other and two transverse yoke elements 5, 6 disposed between them.

A component consisting of the lower transverse yoke element 6 and its attached lower pole shoe 8 with surrounding lower magnetic disk-shaped coil is attached in a fixed position. Relative to this fixed component, a portal consisting of the two vertical yoke elements 3, 4, and a connected upper transverse yoke element 5 with attached upper pole shoe 7 with surrounding upper magnetic coil 9, can be displaced by means of a self-inhibiting spindle drive 11, in order to adjust the width of the space defining the exposure volume 12.

It can furthermore be seen in FIG. 1 that the space defining the exposure volume 12 is limited by bulkheads 14, 15 which limit a slip-in space 13 for a patient. The bulkheads 14, 15 can be adjusted vertically relative to each other in this instance.

Figure 10:
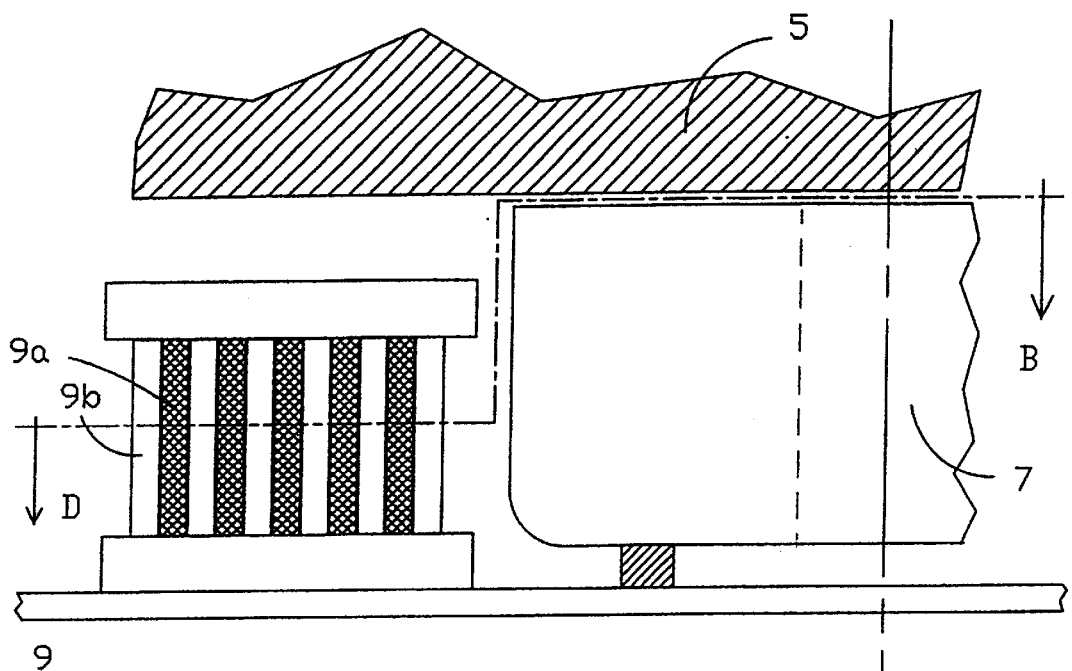
FIG. 10 shows a sectional view through a magnetic coil having heliocoidal windings according to the invention.
Figure 11:
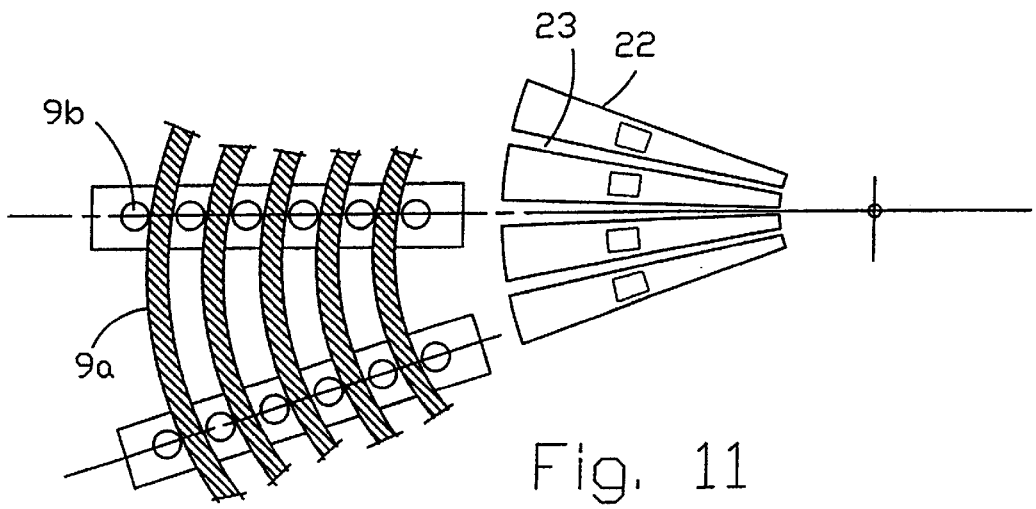
FIG. 11 shows a top plan view of the view of FIG. 10.

As is best depicted in FIGS. 10–11, the upper magnetic coil 9 (and the lower magnetic coil 10) is a disk-shaped coil made of stranded copper wires with one or several windings 9a extending helicoidally, which are separated by ceramic spacer rods 9b.

Figure 8:
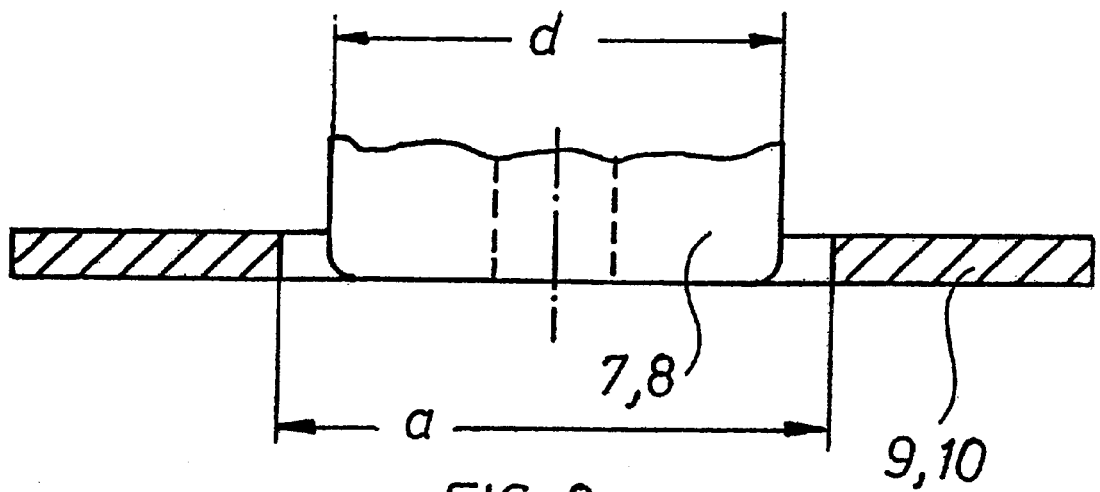
FIG. 8 schematically shows a side view of a magnetic coil flat and flush with a pole shoe surface.

FIG. 8 furthermore shows that the magnetic coils 9, 10 surround the pole shoe ends and create an intermediate air gap (a). As shown in FIG. 4, which shows a top view of one of the pole shoes 7, 8, the pole shoes 7, 8 are designed in a circular shape. The intermediate air gap (a) is of a magnitude range of 0.07 to 0.1 times the pole shoe diameter (d), whereby the magnetic coil is approximately flush-surface with the pole shoe end surface, and the surrounding edge of the pole shoe ends are rounded off.

Furthermore the size of the space defining the exposure volume 12 in FIG. 1, is also designed in consideration of the pole shoe diameter (d) in order to reduce field leakage. Thus the pole shoe diameter (d) should be greater than the space defining the exposure volume 12.

Referring to FIGS. 2 and 3 respectively, shows a lateral view and a top view of the magnetic yoke 2. The magnetic yoke 2 is composed of ferrite segments 16, the surfaces of which are freed of sintering layers and are ground flat on the magnetically conductive surface. These ferrite segments 16 are composed of ferrite plates aligned in rows, as shown in FIG. 6, in the sense of direction of magnetic flow 17.

Referring in more detail to FIG. 6, these ferrite plates 18 are separated from each other perpendicular to the magnetic flow 17 by plastic spacers 20 defining insulation/cooling gaps 19. The ferrite plates 18 are bonded via these plastic spacers 20 to form the ferrite segments 16 that create the yoke elements. Cooling air can be conveyed through the insulation/cooling gap 19 to cool the magnetic yoke 2 as shown schematically in FIG. 6 by means of arrow 21.

Referring now to FIGS. 4 and 5, it can be seen that the round pole shoes 7, 8 are composed of wedge shaped ferrite segments 22 as seen from the top. The surfaces of the segments are also freed of sintering layers and are ground flat. Plastic spacers are also inserted between the wedge-shaped ferrite segments 22 to form insulation/cooling gaps 23, and adjoining ferrite segments are bonded to each other via the spacers to form the circular shaped pole shoes.

It can furthermore be seen in FIGS. 4 and 5 that the pole shoes 7, 8 have an axial, tubular opening 24 that allows cooling air to be introduced into the magnetic field applicator 1, seen in FIG. 1.

Referring now to FIG. 7, the ferrite segments 16 adjoin each other along the magnetic flow direction 17 by way of narrow transition gaps ($S_2$). As can also be seen in FIG. 7, forced-air gaps ($S_1$) are provided at the transitions between the vertical yoke elements 3, 4 which are adjustable relative to the lower transverse yoke element 6, as well as the transitions between the transverse yoke elements 5, 6 and the pole shoes 7, 9, for advantageous control of the magnetic flow. These forced-air gaps ($S_1$) have a gap width of approximately 2 to 3 mm and are very large in comparison to the narrow transition gaps ($S_2$).

The magnetic field is produced by the magnetic coils 9, 10, connected to a capacitor and an oscillatory circuit in which the energy oscillates as an idle power at the resonance frequency of the circuit. The magnetic field forces are preferably in a range of 1 to 20 kA/m, while the frequencies are preferably in a range of 20 to 500 kHz. In a thermoseed application of the magnetic field applicator according to the invention, 1 to 2 kA/m is sufficient, while higher field forces are necessary in applications using magnetic fluids.

Figure 9:
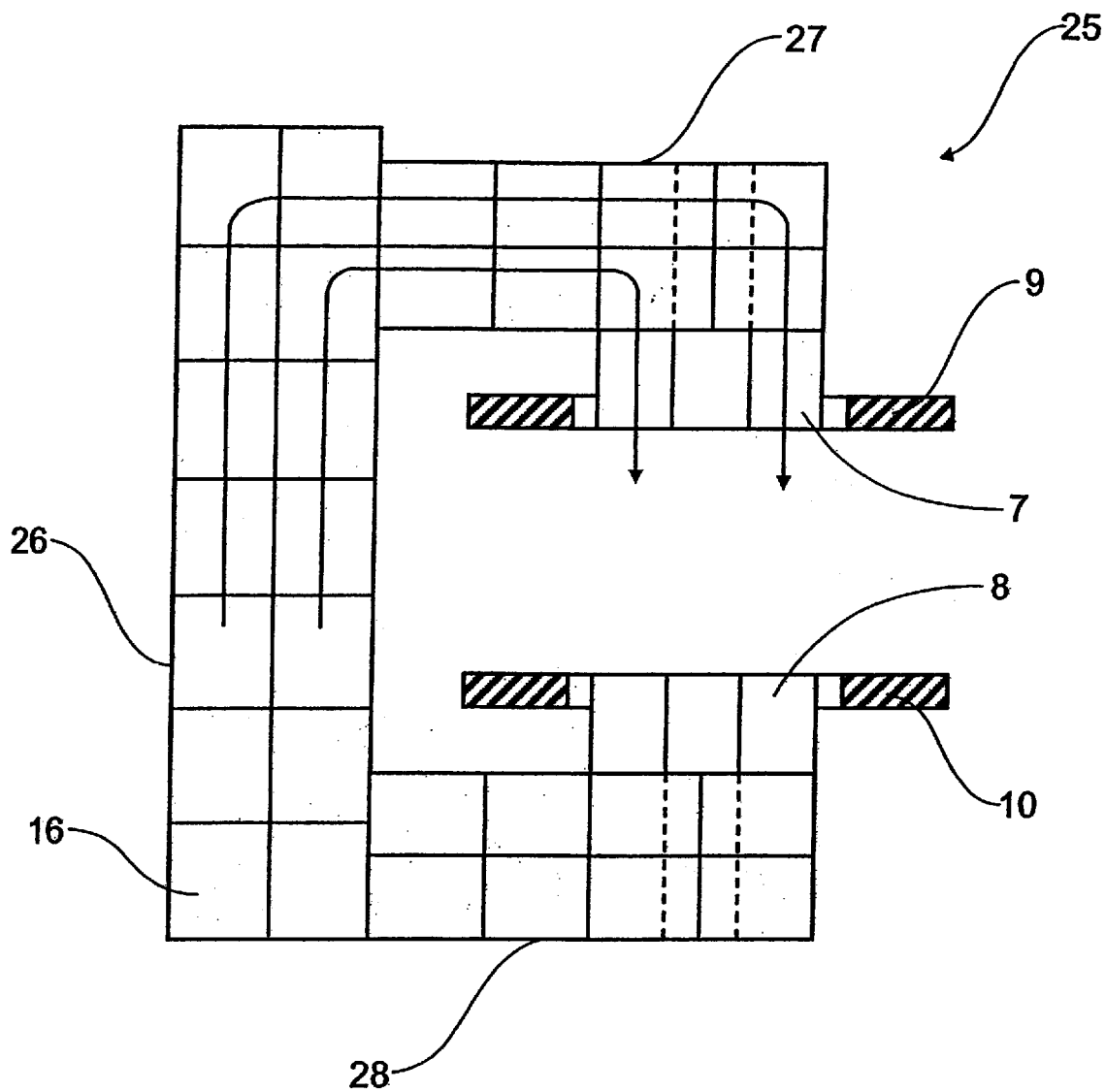
FIG. 9 shows a side view of another embodiment of magnetic field application according to the invention having a "C" shape.

Referring now to FIG. 9, an alternative embodiment of a magnetic yoke 25 in the form of a C-arc is shown. This C-arc comprises a vertical yoke element 36 and an upper transverse yoke element 27 as well as a lower transverse yoke element 28. With the exception of the C design shape, the magnetic yoke 25 is constructed with the same components as the magnetic yoke shown in FIG. 2, so that the same parts are designated with the same references. Thus the vertical yoke element 26, the upper transverse yoke element 27 and the lower transverse yoke element 28 are constructed out of ferrite segments 16, and the magnetic yoke 25 with corresponding pole shoes 7, 8 have their respectively assigned magnetic disk shaped coils 9, 10. A C-arc of this type has the advantage of excellent accessibility to the magnetic field and components, but has the disadvantage of a larger field leakage, and is therefore a less efficient embodiment.

While a preferred embodiment of the invention has been described using specific terms, such description is for illustrative purposes only, and it is to be understood that changes and variations may be made without departing from the spirit and scope of the claims below. Other embodiments and modifications may become apparent to those skilled in the art upon reading the foregoing specification, but such modifications and embodiments may be within the scope of the invention which is limited only by the claims below.

What is claimed is:

1. A magnetic field applicator for heating magnetizable materials in biological tissue of the type that includes a magnetic yoke with two pole shoes facing each other separated by a gap to create an exposure volume, and a magnetic coil for the production of a magnetic alternating field associated with each pole shoe, wherein the applicator comprises:

a magnetic yoke having two parallel vertical yoke elements spaced a distance from each other and two transverse yoke elements connected between said vertical yoke elements;

opposed pole shoes disposed generally in the center of said transverse yoke elements;

at least one transverse yoke element being displaceable relative to the other of said transverse yoke elements so that the gap defining the exposure volume may be adjusted;

said magnetic yoke being constructed from a plurality of ferrite segments joined together;

said magnetic alternating fields having magnetic field forces of about 10 to 15 kA/m and frequencies of about 50 to 100 kHz generated by said applicator; and said magnetic coils are disk coils with at least one winding extending helicoidally, each said magnetic coil surrounding a respective pole shoe to define an intercalated surrounding magnetic coil/pole shoe gap.

2. The applicator of claim 1 wherein said two transverse yoke elements include a lower transverse yoke element which carries said pole shoe and surrounding magnetic coil and a portal including said two vertical yoke elements and an upper transverse yoke element which carries said opposing pole shoe and surrounding magnetic coil and a vertical adjustment device for displacing said portal relative to said lower transverse yoke element to adjust the gap of the exposure volume.

3. The applicator of claim 2 wherein said vertical adjustment device consists of at least one motor-controlled linear drive operatively connected for moving said vertical yoke elements.

4. The applicator of claim 1 wherein said magnetic yoke is carried within a supporting structure into which cooling air can be caused to flow.

5. The applicator of claim 1 wherein said exposure volume is delimited on the side by said vertical yoke elements and can be further delimited by spaced, vertical bulkheads which define a slide-in chamber.

6. The applicator of claim 1 wherein said magnetic coils have one or more extending helicoidally windings made of stranded copper wires.

7. The applicator of claim 6 wherein said pole shoes are circular and oppose each other with parallel circular pole shoe surfaces separated to define the gap of the exposure volume; wherein said magnetic coils are made in form of corresponding circular rings.

8. The applicator of claim 1 wherein said magnetic coil/pole shoe gap is in a range of 0.07 to 0.1 times the pole shoe diameter; the surface of the magnetic coils is approximately flush with the pole shoe end surface; and includes a rounded surrounding edge formed around said pole shoe end surface.

9. The applicator of claim 1 wherein said pole shoe has a diameter which is greater than the exposure volume gap.

10. The applicator of claim 1 wherein said magnetic yoke comprised of cut ferrite yoke segments having surfaces which are ground free of sintering and to be planed parallel; and said round pole shoes are composed of machined ferrite pole segments that are wedge-shaped.

11. The field applicator of claim 10, including pole separators inserted between said wedge-shaped pole segments in order to create cooling gaps; and an axial tubular opening is provided to form a tubular pole shoe through which cooling air can be caused to flow.

12. A magnetic field applicator for heating magnetizable materials in biological tissue of the type that includes a magnetic yoke with two pole shoes facing each other separated by a gap to create an exposure volume, and a magnetic coil for the production of a magnetic alternating field associated with each pole shoe, wherein the applicator comprises:

- a magnetic yoke having two parallel vertical yoke elements spaced a distance from each other and two transverse yoke elements connected between said vertical yoke elements;
- opposed pole shoes disposed generally in the center of said transverse yoke elements;
- at least one transverse yoke element being displaceable relative to the other of said transverse yoke elements so that the gap defining the exposure volume may be adjusted;
- said magnetic yoke being constructed from a plurality of ferrite segments joined together;
- said magnetic yoke comprised of cut ferrite yoke segments having surfaces which are ground free of sintering and to be planed parallel; and said round pole shoes are composed of machined ferrite pole segments that are wedge-shaped; and
- said yoke segments include ferrite plates arranged in a row in the direction of magnetic flow, said yoke segments being spaced from each other transverse to the direction of magnetic flow to define cooling gaps 19 through which cooling air can be conveyed; and which adjacent ones of said yoke segments adjoin each other in the direction of magnetic flow via a narrow contact gap.

13. The applicator of claim 12, including plastic separators inserted disposed in said cooling gaps between adjacent ferrite plates wherein said ferrite plates are bonded together via the separators into said yoke elements.

14. The applicator of claim 12 including contact gaps defined between adjacent yoke elements, and transition gaps defined between said transverse yoke elements and said vertical yoke elements which are adjustable relative to each other to define forced air gaps to control the magnetic flow; and said forced-air gaps having a width greater than said contact gaps.

15. A magnetic field applicator for heating magnetizable materials in biological tissue of the type that includes a magnetic yoke with two pole shoes facing each other separated by a gap to create an exposure volume, and a magnetic coil for the production of a magnetic alternating field associated with each pole shoe, wherein the applicator comprises:

- a magnetic yoke having two parallel vertical yoke elements spaced a distance from each other and two transverse yoke elements connected between said vertical yoke elements;
- opposed pole shoes disposed generally in the center of said transverse yoke elements;
- at least one transverse yoke element being displaceable relative to the other of said transverse yoke elements so that the gap defining the exposure volume may be adjusted;
- said magnetic yoke being constructed from a plurality of ferrite segments joined together;
- said magnetic yoke comprised of cut ferrite yoke segments having surfaces which are ground free of sintering and to be planed parallel; and
- said round pole shoes are composed of machined ferrite pole segments that are wedge-shaped; and
- including pole separators inserted between said wedge-shaped pole segments in order to create cooling gaps; and an axial tubular opening is provided to form a tubular pole shoe through which cooling air can be caused to flow.

* * * * *